(12) United States Patent
Moeckli et al.

(10) Patent No.: US 7,242,479 B2
(45) Date of Patent: *Jul. 10, 2007

(54) GAS SENSORS

(75) Inventors: Marc Andreas Moeckli, Egg (CH);
Urs Frederich Boegli, Esslingen (CH);
Len John Blatnica, New Kensington, PA (US); Philipp Albert Bachmann, Forch (CH); Hans Trachsel, Uetikon (CH)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/408,363

(22) Filed: Apr. 21, 2006

(65) Prior Publication Data
US 2006/0192966 A1     Aug. 31, 2006

Related U.S. Application Data

(63) Continuation of application No. 09/611,384, filed on Jul. 7, 2000, now Pat. No. 7,034,943.

(51) Int. Cl.
*G01N 21/00* (2006.01)
*G01N 21/35* (2006.01)
*G01H 17/00* (2006.01)

(52) U.S. Cl. .................. 356/437; 356/432; 356/433; 250/343; 250/339.04; 73/24.02

(58) Field of Classification Search ........ 356/432–437, 356/71–73; 250/215, 227.11, 339.07, 343; 250/339.08, 252.1, 352, 339.13, 231.14; 73/24.02, 579, 61.75

See application file for complete search history.

(56) References Cited

U.S. PATENT DOCUMENTS 4,436,428 A * 3/1984 Watanabe et al. ........... 356/432

(Continued)

Primary Examiner—Sang H. Nguyen
(74) Attorney, Agent, or Firm—JamessG. Uber; Henry E. Bartony, Jr.

(57) ABSTRACT

The present invention relates to a device for accomplishing noise reduction in a photoacoustic gas detector using a sound damping element and/or a background or reference microphone where a preferably larger external volume that acts as a sound damping element (SDE) is coupled to a smaller volume through which the gas diffuses. The coupling is accomplished in such a way that the externally generated sound waves incident upon the photoacoustic detector are adequately attenuated by the larger volume SDE without adversely affecting diffusion of the gaseous species of interest through the smaller volume for measurement by the detector. Preferably this is accomplished by coupling the larger SDE volume to the smaller gas diffusion volume by a long and thin pressure channel. Another photoacoustic detector includes a measuring system to measure the photoacoustic excitation of analyte gas entering the photoacoustic detector, a reference system to measure the effect of pressure waves in the environment, and a system for offsetting an output from the measuring system with an output from the reference system to reduce noise resulting from pressure waves in the environment in an output signal of the photoacoustic detector. The present invention also relates to a device for testing the integrity of a porous member and includes a source of pressure waves and a sensor for measuring a signal resulting from the transmittal of pressure waves from the transmitter. The signal is proportional to pressure losses through the porous member. The pressure losses through the porous member are, in turn, a measure of the degree to which the porous member has become clogged.

3 Claims, 8 Drawing Sheets

U.S. PATENT DOCUMENTS 4,622,845 A * 11/1986 Ryan et al. ................. 73/24.02
5,616,826 A *  4/1997 Pellaux et al. ............. 73/24.02
6,006,585 A * 12/1999 Forster ...................... 73/24.01
6,049,728 A *  4/2000 Chou ......................... 600/316

* cited by examiner

GAS SENSORS

CROSS-REFERENCE TO RELATED APPLICATIONS

This application is a continuation of U.S. patent application Ser. No. 09/611,384 filed on Jul. 7, 2000 now U.S. Pat. No. 7,034,943.

FIELD OF THE INVENTION

The present invention relates generally to gas sensors, and, especially, to devices and methods for increasing signal-to-noise ratios in photoacoustic detectors and other gas sensors.

BACKGROUND OF THE INVENTION

The use of diffusive gas sensors to detect the concentration level of gaseous species of interest using the photoacoustic effect is well known. For example, U.S. Pat. No. 4,740,086 teaches the use of a diffusive photoacoustic gas sensor to convert the optical energy of an amplitude modulated light source into acoustic energy when the light mechanically and thermally excites the gaseous species of interest as it diffuses into a sensing chamber upon which the light is incident. Sound waves of an intensity corresponding to the concentration level of the gas within the chamber are generated as the light radiation absorbed by the gas creates pressure fluctuations of a magnitude proportional to the number of gas molecules located within the sensing chamber. These sound/pressure waves are detected by an acoustic detector such as a microphone.

However, the output signal of a diffusive photoacoustic sensor is susceptible to noise created by interference from outside sources of air pressure fluctuations, such as wind, vibration and acoustic phenomena. To eliminate such noise, one may incorporate some means of attenuating extraneously generated pressure waves, while attempting to allow the gas to freely diffuse into the sensing chamber for detection. For example, porous members through which gas relatively readily diffuses, but which attenuate the effect of external pressure fluctuations, are often placed at the entrance of photoacoustic sensors. However, one must balance this attenuating effect with an increase in response time. In that regard, introduction of a sound/pressure attenuating element(s) to reduce noise typically results in a corresponding loss of responsiveness to changing signal levels. The specifications for combustible gas detectors of the Instrument Society of America (ISA) require gas concentration level measurement stability at wind speeds of up to 5 meters per second (m/s) with a corresponding response time (to 60% of full scale indication) of less than 12 seconds.

It is very desirable to develop devices and methods that increase signal-to-noise ratios in photoacoustic detectors and other gas sensors while maintaining a satisfactory response time for such detectors.

SUMMARY OF THE INVENTION

In one aspect, the present invention provides a sound/pressure damping element (SDE) designed for use in a diffusive, non-resonant photoacoustic gas sensor (detector). The SDE reduces external, low-frequency noise to acceptable levels while permitting the photoacoustic detector (sensor) to maintain an adequate response time to changing gas concentration levels.

In general, the photoacoustic detector includes a first volume having a sensor system for photoacoustic detection therein. The first volume is in fluid connection with the environment through an opening so that the gas analyte can diffuse into the first volume through the opening. The photoacoustic detector further includes a second volume (an SDE volume) in connection with the first volume such that pressure readily equalizes between the first volume and the second volume and such that diffusion of analyte gas from the first volume to the second volume is hindered (or slowed as compared to diffusion of analyte gas into the first volume from the environment).

As in current photoacoustic detectors, sound waves of an intensity corresponding to the concentration level of the analyte gas within the first volume or sensing chamber are generated as the optical energy of the light incident upon the sensing chamber is converted into acoustic energy upon absorption by the analyte gas, causing mechanical excitation of the analyte gas molecules which generates air pressure fluctuations of an intensity proportional to the number of analyte gas molecules located within the sensing chamber. The sound waves are then detected by a detector such as a microphone.

Preferably, the second volume is larger than the first volume to enhance attenuation of external pressure fluctuations. The first volume may, for example, be connected to the second volume by a channel that is shaped to limit diffusion of analyte gas therethrough. The channel may, for example, be elongated and of small cross section compared to the opening into the first volume.

In one embodiment, the photoacoustic detector includes a first volume having a sensor system for photoacoustic detection therein. The first volume is in fluid connection with a second volume via a porous member (for example, a sintered disk) through which the analyte gas can readily diffuse. The second volume is in fluid communication with the environment via a second porous member through which the analyte gas can readily diffuse. The second volume is in connection with a third volume in a manner that pressure readily equalizes between the third volume and the second volume, but that diffusion of analyte gas from the second volume to the third volume is hindered as describe above.

In another aspect, the present invention provides a photoacoustic detector including a measuring system to measure the photoacoustic excitation of analyte gas entering the photoacoustic detector, a reference system to measure the effect of pressure waves in the environment, and a system for offsetting an output from the measuring system with an output from the reference system to reduce noise resulting from pressure waves in the environment in an output signal of the photoacoustic detector. The measuring system can, for example, include a first microphone to measure photoacoustic excitation of gas; and the reference system can include a second microphone to measure an offset signal that is processed by the system electronics to reduce the effect of externally generated pressure waves on the output signal of the photoacoustic sensor. The reference system can, for example, be disposed within an SDE volume as described above. The first microphone can also be disposed within a photoacoustic cell, and the second microphone can be disposed within a reference cell. The photoacoustic cell and the reference cell are preferably well matched (for example, of generally the same volume).

In a further aspect, the present invention provides a photoacoustic detector including a measuring cell, a reference cell and a pressure gradient microphone coupled between the two cells. The pressure gradient microphone measures the pressure difference between the measurement cell and the reference cell to reduce noise from external pressure waves in an output of the photoacoustic sensor.

In another aspect, the present invention provides a device for testing the integrity of a porous member. The device includes generally a source of pressure waves and a sensor for measuring a signal resulting from the transmittal of pressure waves from the transmitter. The signal is proportional to pressure losses through the porous member. The pressure losses through the porous member are, in turn, a measure of the degree to which the porous member has become clogged.

In still another aspect, the present invention provides a sensor for the detection of an analyte in an environment, the sensor includes a porous member positioned over an inlet of the sensor and a system for testing the integrity of the porous member as described above.

Other details, objects, and advantages of the present invention will become apparent in the following description of the presently preferred embodiments.

DETAILED DESCRIPTION OF THE INVENTION

Figure 1:
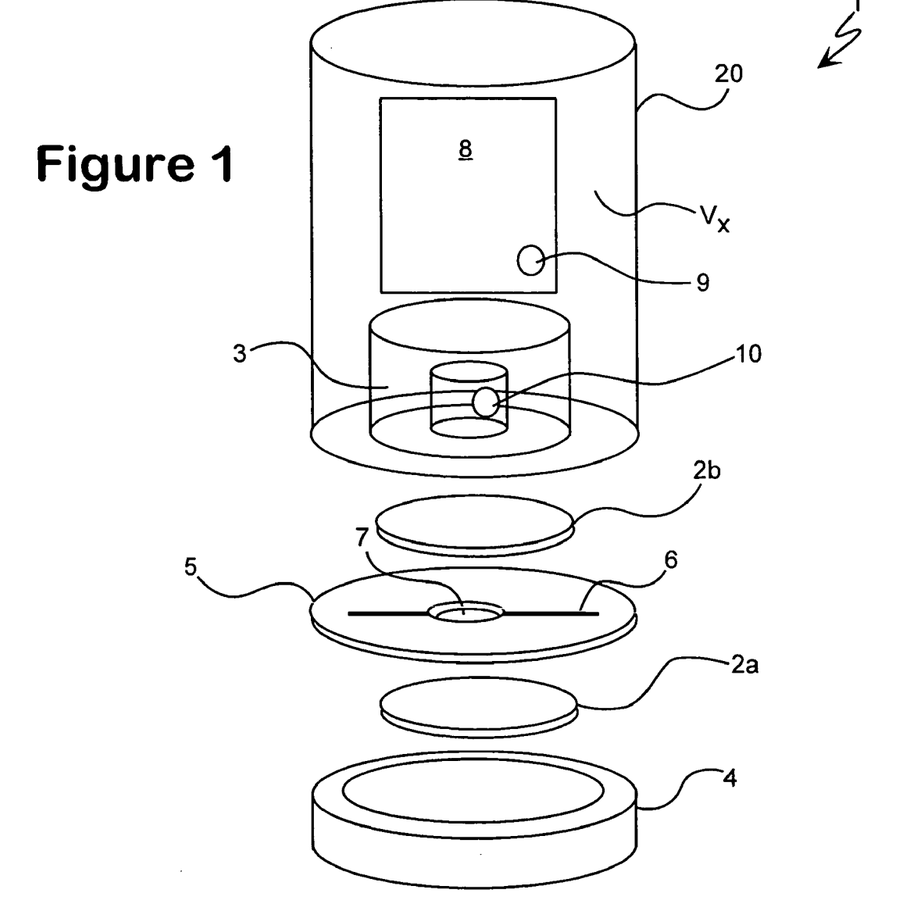
FIG. 1 is a perspective view of a photoacoustic detector of the present invention in a partially disconnected state.

An embodiment of a diffusive, non-resonant photoacoustic methane detector of the present invention is illustrated in FIG. 1. Reference is made to U.S. Pat. No. 4,740,086, the disclosure of which is incorporated by reference as if fully set forth herein, for the general principles of operation and construction of a photoacoustic sensor/detector. In the embodiment of FIG. 1, an opening within gas inlet 4 of photoacoustic detector 1 is preferably covered with a porous material such as a first metal sinter disk 2a, which permits the diffusion of molecules of the gas species of interest (that is, the analyte gas or gases) into sensing (or measurement) cell 3 of photoacoustic detector 1. As known in the art, first sinter disk 2a acts to attenuate external sources of pressure waves by impeding the progress of air pressure waves incident upon gas inlet 4, while offering only minimal resistance to the diffusion of gas molecules into photoacoustic detector 1 from gas inlet 4. In the embodiment of FIG. 1, a second sinter disk 2b also acts to attenuate external sources of pressure waves by further impeding the progress of any air pressure waves that pass through the first sinter disk 2a. Like sinter disk 2a, sinter disk 2b preferably offers only minimal resistance to the diffusion of gas molecules into measurement cell 3 of photoacoustic detector 1.

Figure 2:
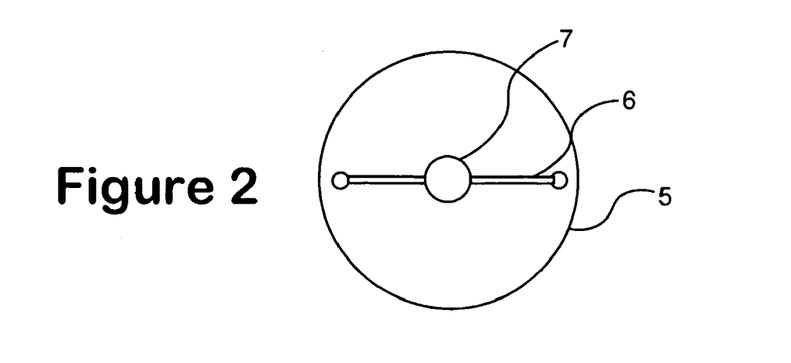
FIG. 2 is a plan view of a pressure coupling suitable for use in the photoacoustic detector of FIG. 1.
Figure 3:
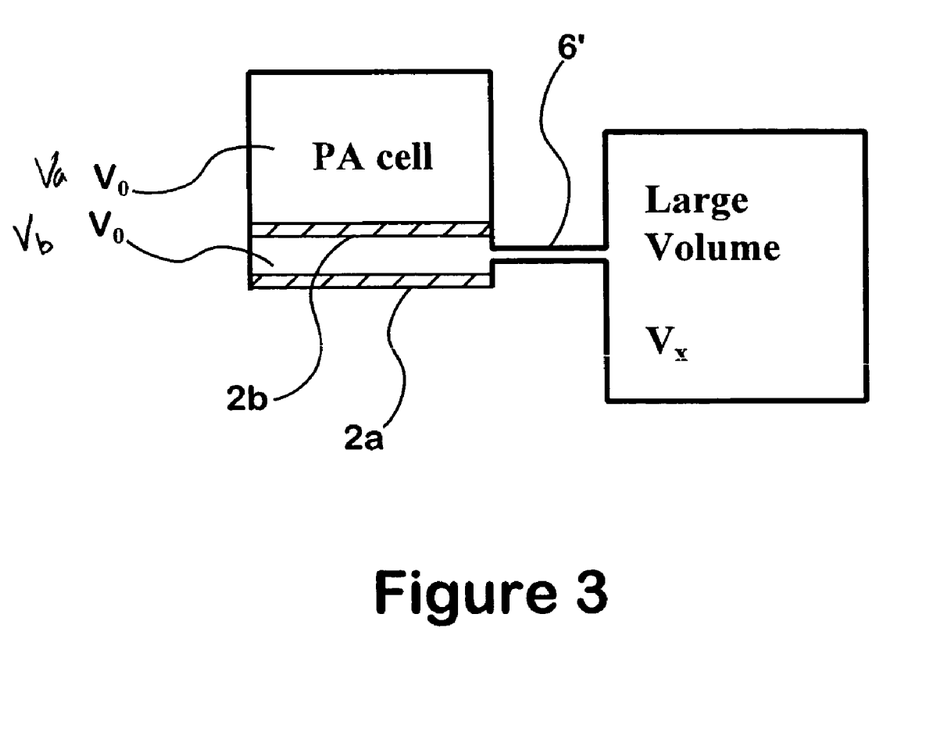
FIG. 3 is a schematic depiction of another embodiment of a pressure coupling of an external sound/pressure damping volume to a sensing volume or cell.

While allowing the gas to diffuse into measurement cell 3, sinter disks 2a and 2b act to enclose an incident external pressure wave within the area defined by the space therebetween ($V_b$), which, along with the area defined by the measurement cell 3, ($V_a$), forms a gas diffusion volume $V_o$ ($V_a+V_b$) as best shown in FIG. 3. Volume $V_o$ is preferably kept as small as possible to minimize the amount of time required for the gas analyte to diffuse into measurement cell 3. In the embodiment of FIGS. 1 and 2, a disk 5, preferably fabricated from teflon or a similar material, occupies the space between sinter disks 2a and 2b to connect the volume between the sinter disks 2a and 2b with an SDE volume $V_x$ (external to the sensing volume of measurement cell 3) defined generally by housing 20. Unlike sinter disks 2a and 2b, disk 5 offers only small resistance to pressure waves as a result of the presence of capillary slits 6 (corresponding to pressure channel 6' in the embodiment of FIG. 3 discussed below) to form a path for the passage of external sound/pressure waves into SDE volume $V_x$. A hole 7 located at the center of disk 5 serves as the path for diffusion of the analyte gas molecules through disk 5 as they pass into measurement cell 3. Slits 6 are preferably made to have relatively small cross-sectional area as compared to the area of inlet hole 7 and to be relatively long so that analyte gas molecules diffuse through slits 6 at a much slower rate than analyte gas molecule diffuse through sinter disks 2a and 2b and through hole 7.

SDE volume $V_x$ absorbs energy of an incident external pressure wave that passes first sinter disk 2a and thus reduces the pressure amplitude of the noise signal resulting from the incident pressure wave. Other than the fluid connection of slits 6 to the environment, $V_x$ is preferably pressure tight to prevent external pressure waves from entering photoacoustic detector 1 by any path other than through sinter disks 2a and 2b. $V_x$ is preferably relatively large as compared to $V_o$. In that regard, the larger $V_x$ is compared to $V_o$, the greater the percentage of the energy of incident pressure fluctuation that is absorbed by $V_x$. Preferably, $V_x$ is at least approximately 2 times as large as $V_o$. More preferably, $V_x$ is at least approximately 5 times as large as $V_o$. Most preferably, $V_x$ is at least approximately 10 times as large as $V_o$.

In another aspect of the present invention, $V_x$ also provides space for a secondary microphone 9 that can be placed into volume $V_x$ to measure noise levels generated by incident external pressure wave energy, allowing generation of a measurement compensating signal that can be processed by conventional signal processing circuitry 8 in conjunction with the signal from primary microphone 10 (used to measure the photoacoustically generated signal) to further reduce or eliminate the effect of external pressure changes on the overall output signal provided by photoacoustic detector 1.

As in photoacoustic sensors in general, sound waves of an intensity corresponding to the concentration level of the analyte gas are generated when optical energy from light incident upon sensing chamber 3 is converted into acoustic energy upon absorption by the analyte gas, causing mechanical excitation of the analyte gas molecules to generate air pressure fluctuations of an intensity proportional to the number of gas molecules located within sensing cell 3. The sound waves are detected by microphone 10. Referring to, for example, FIG. 3, the coupling of external volume $V_x$ to preferably smaller gas diffusion volume $V_o$ acts to cause sound/pressure damping in such a way that the externally generated pressure waves incident upon the photoacoustic detector are adequately attenuated by the preferably larger volume $V_x$ without adversely affecting diffusion of the gaseous species of interest through $V_o$ for measurement by the detector. As discussed above, this result can be accomplished by attaching the preferably larger volume $V_x$ to the smaller gas diffusion volume (defined, in part, by sinter disks 2a and 2b) by a pressure channel 6' that is preferably both relatively long and relatively thin (that is, of relatively small cross section). Channel 6' acts like a capillary such that gas molecules diffuse at a much lower rate through pressure channel 6' than through porous membranes/sinter disks 2a and 2b, whereas pressure channel 6' offers almost no resistance to the passage of external pressure waves into SDE volume $V_x$ at the low frequencies experienced by the photoacoustic sensors of the present invention. The low resistance to sound/pressure waves offered by pressure channel 6' causes volume $V_x$ to receive and adequately attenuate the external sound/pressure wave energy incident upon gas diffusion volume $V_o$ without detrimentally increasing the response time of the sensor, since the number of gas molecules lost to volume $V_x$ is minimized by the low diffusion rates through pressure channel 6'.

The attenuating effect of volume $V_x$ can be explained through the model discussed below. An external pressure wave first penetrates first sinter disk 2a and results in a pressure increase $\Delta P$ in the small volume $V_b$ between sinter disks 2a and 2b. The pressure difference is equalized through pressure channel 6'. The equalization of the pressure difference corresponds to an adiabatic expansion of the air between the sinter disks into $V_x$. The pressure increase that is finally detected by microphone 10, in the measurement cell is thus the original pressure increase $\Delta P$ multiplied by a factor equivalent to $[V_o/(V_x+V_o)]$. As discussed above, $V_o$ is the sum of the volume $V_b$ between the metal sinters disks 2a and 2b and the volume $V_a$ of sensing cell 3 of photoacoustic detector 1. Therefore, the larger an external volume $V_x$ that is coupled to volume $V_o$, the smaller the factor $V_o/(V_x+V_o)$ will be.

Figure 4:
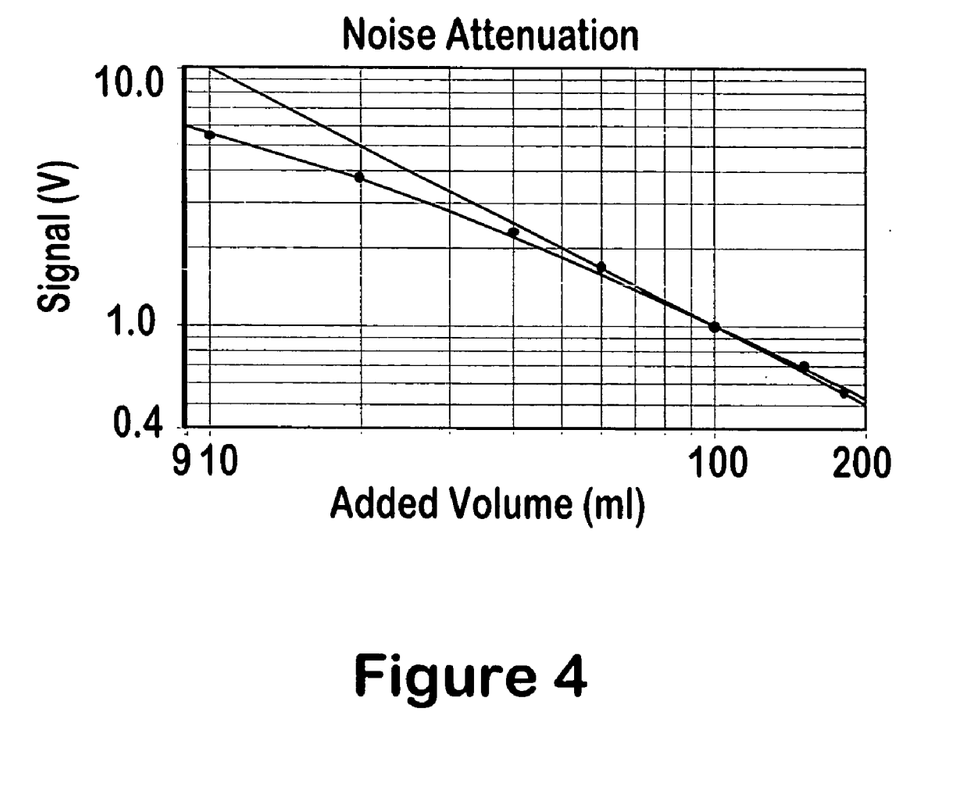
FIG. 4 is a graph showing the effect of attenuating externally generated pressure waves by coupling an external sound/pressure damping volume to the sensing volume.

The above model correlates well with the increased attenuation of externally generated pressure waves with increasing external volume $V_x$ as shown in FIG. 4. FIG. 4 illustrates an example of the attenuation of an external sound wave at 6 Hz with increasing SDE volume $V_x$. For ease of experimentation, the photoacoustic sensors in these studies were designed as depicted in FIG. 3 so that volume $V_x$ could be more easily varied. In the studies of FIG. 4, the photoacoustic detectors included two identical sinter disks 2a and 2b of approximately 0.062 inch thickness that were separated by approximately 11 mm and glued on a cylindric metal ring with an approximately 24 mm inner diameter. The volume between sinter disks 2a and 2b was coupled to a variable external volume $V_x$ via of tubing of approximately 50 cm length and with an approximately 4 mm inner diameter. The sensor was then irradiated with a sound wave at 6 Hz that was generated with a loudspeaker. As SDE volume $V_x$ increased, the detected noise amplitude decreased by a factor of $V_o/(V_x+V_o)$. By adding an external volume of approximately 200 ml, the noise amplitude was observed to decrease by a factor of approximately 10 from its initial value (see FIG. 4).

In one embodiment of photoacoustic detector 1 used in the studies of the present invention, SDE volume $V_x$ was incorporated into the housing of an ULTIMA® model gas sensor available from Mine Safety Appliances Company of Pittsburgh, Pa. In this embodiment, disk 5 was made of an approximately 0.6 millimeter (mm) thick Teflon membrane with a slit 6 that was approximately 1 mm in width. Sinter disk 2a had a thickness of approximately 0.062 inches and sinter disk 2b had a thickness of approximately 0.02 inches. Each of sinter disks 2a and 2b had a pore size (diameter) of approximately 0.1 micron. A Panasonic microphone model WM-034 was used for each of primary microphone 10 and the secondary microphone 9. An ALBA lamp model 7328 was operated at an 8 hertz (Hz) square wave pulse frequency with an amplitude of 5 volts (V) to generate an amplitude modulated light signal that was incident on the photoacoustic detector 1. As is clear to one skilled in the art, some or all of the components of photoacoustic detector 1 may be embodied in alternative ways. For example, sinter disks 2a and 2b can be replaced by a gas transparent membrane. An alternative to pressure channel 6' or slits 6 to connect $V_x$ with $V_o$ is a gas tight flexible membrane that is transparent to the passage of sound/pressure waves but prevents or hinders the diffusion of gas molecules.

Figure 5:
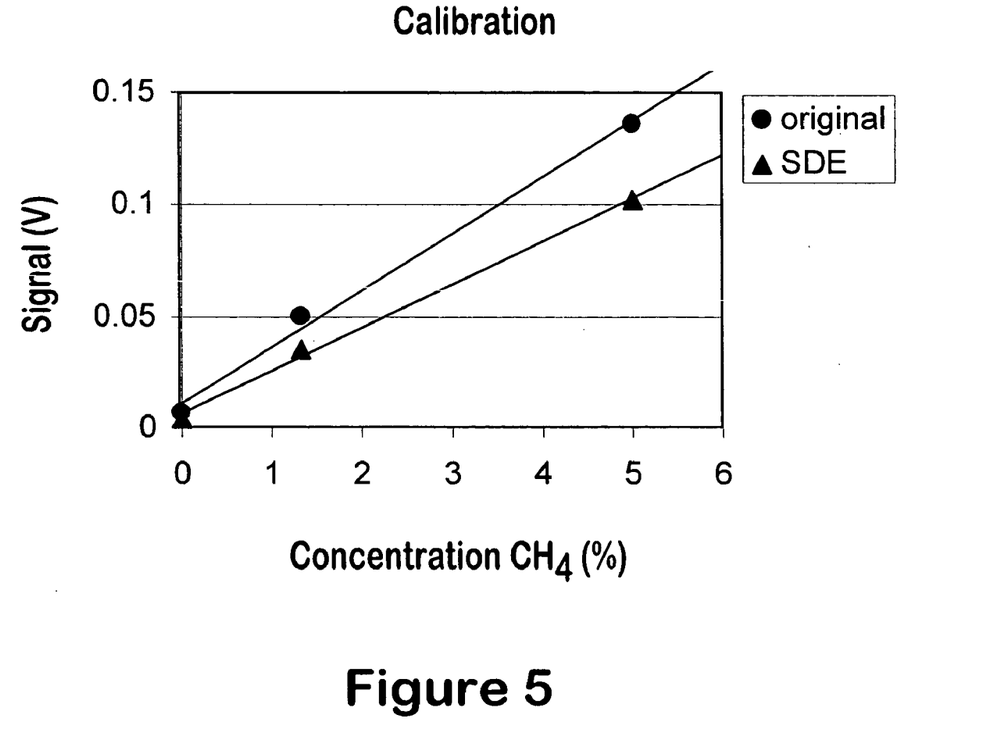
FIG. 5 is a graph showing a comparison of calibration curves of photoacoustic cells with and without an external sound/pressure damping volume.

In several other studies with such photoacoustic sensors, the photoacoustic sensors were tested both with and without the installation/connection of an SDE volume $V_x$. In these studies, the sensors were calibrated with ambient air (0% $CH_4$), with 1.33% $CH_4$ (27% LEL—lower explosion limit) and with 5% $CH_4$ (100% LEL). As shown in FIG. 5, a good linear relation between the applied gas concentration and the resulting signal output (voltage in the study of FIG. 5) was achieved both with and without SDE volume $V_x$. The output signal at 5% methane was believed to be smaller when volume $V_x$ was installed as a result of an increased signal pressure loss through the 0.02 inch thick second sinter disk 2b used in these studies as compared to the corresponding "conventional" sensor (that is, a sensor without volume $V_x$ and without second sinter disk 2b—wherein the cell is separated from the ambient environment by only first sinter disk 2a). The thickness of sinter disk 2a in the "conventional" sensor was 0.062 in, which is the same as the thickness of disk 2b in the sensor of the present invention.

Figure 7:
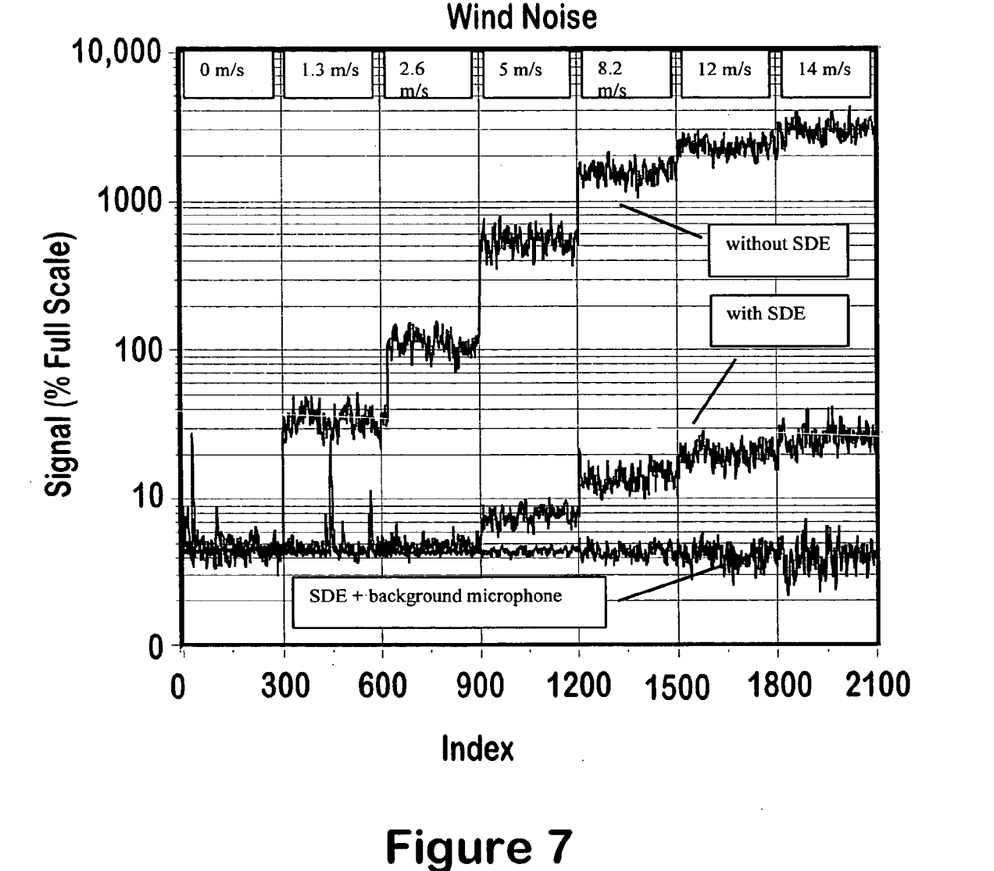
FIG. 7 is a graph showing a comparison of the wind noise reduction characteristics of photoacoustic cells constructed (i) without an external sound/pressure damping volume, (ii) with an external sound/pressure damping volume, and (iii) with both an external sound/pressure damping volume and a background/reference microphone.

In these studies, the microphone signal was preamplified and sampled with a computer analog-to-digital (A/D) converter card at a rate of 4096 Hz. A lock-in program was then used for the calculation of the signal amplitude and phase with respect to a reference frequency of 8 Hz. The implemented lock-in algorithm detected frequency components at the reference frequency and (attenuated) at its odd higher harmonics. To characterize the lock-in algorithm, a sine wave signal with a constant peak-to-peak amplitude of 50 mV and increasing frequency was applied to the microphone preamplifier. The detection bandwidth was 9 Hz FWHM (full width at half maximum) at the fundamental frequency of 8 Hz. When a background/reference microphone 9 was used, both the signal from measurement cell microphone 10 and background microphone 9 were passed through the lock-in program individually. The resulting concentration value from the background microphone 9 was scaled and then subtracted from the concentration value of the measurement cell microphone 10. The additional noise reduction resulting from subtraction of the output of microphone 9 is illustrated in FIG. 7.

Figure 6:
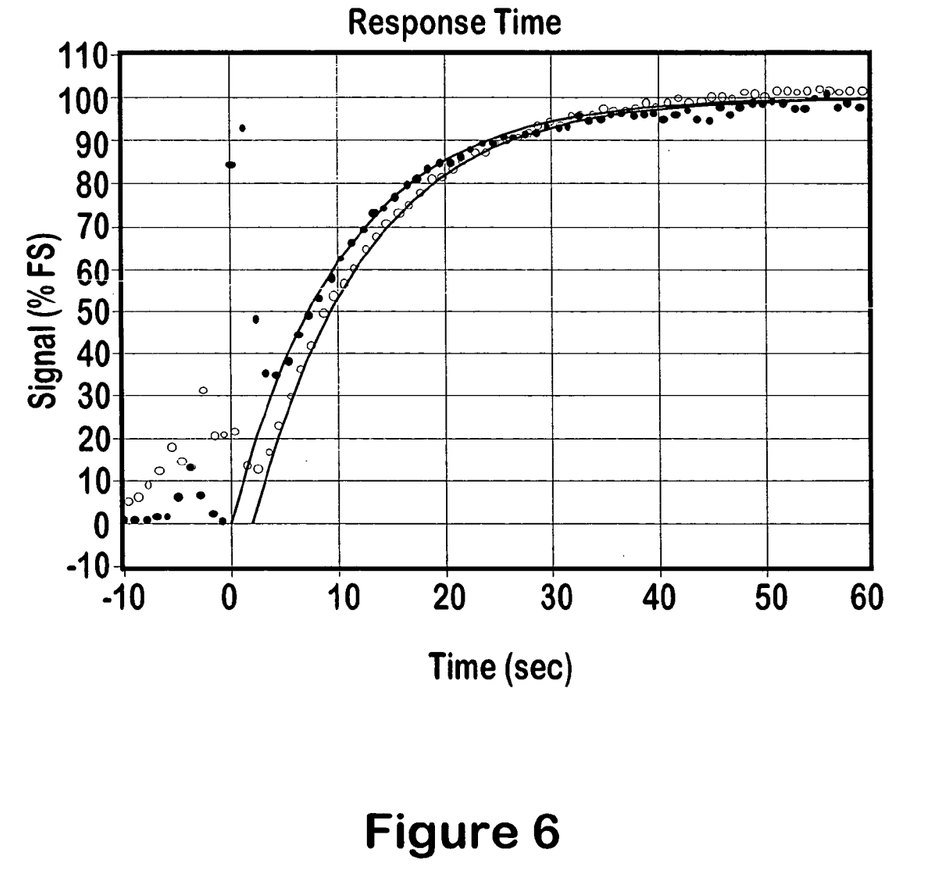
FIG. 6 is a graph showing a comparison of response times of a sensor equipped with an external sound/pressure damping volume (unfilled circles) and a sensor without an external sound/pressure damping volume (filled circles).

The response time of the experimental system used in the studies of FIG. 4 exceeded the ISA requirements. However, by minimizing the distance between the sinter disks and reducing the thickness of the sinter disks, substantially shorter response times can be obtained while the noise attenuating effect is maintained. In several studies of photoacoustic sensors of the embodiment illustrated in FIG. 1, for example, the thickness of inner sinter disk 2b was reduced to approximately 0.02 inches and the distance between disks 2a and 2b was minimized. FIG. 6 demonstrates that the response time of the photoacoustic sensors 1 of FIG. 1 ($T_{60}$=11.5 sec; represented by unfilled circles in FIG. 6) meets the ISA requirement and is only slightly greater than a conventional configuration (that is, the sensor of FIG. 1 without an SDE—without second sinter disk 2b and without membrane 5) as represented by the filled circles in FIG. 6 ($T_{60}$=8.5 sec). The response time was determined by placing the sensor inlet into a volume that contained a gas concentration of 5% methane (full scale). The lower explosion limit or LEL of methane is 5%. On the other hand, the noise attenuating effect of the SDE is demonstrated in FIG. 7. Whereas the noise level in the embodiment of FIG. 1 remains below 10% at 5 m/s wind speed (satisfying ISA requirements), the noise level in the setup without SDE already exceeds 100% full scale indication at a wind speed of 2.6 m/s. When the data of background microphone 9 was used in addition to the SDE effect, the noise level of the output signal could be reduced below 10% full scale up to wind speeds of 14 m/s (see FIG. 7).

Figure 8:
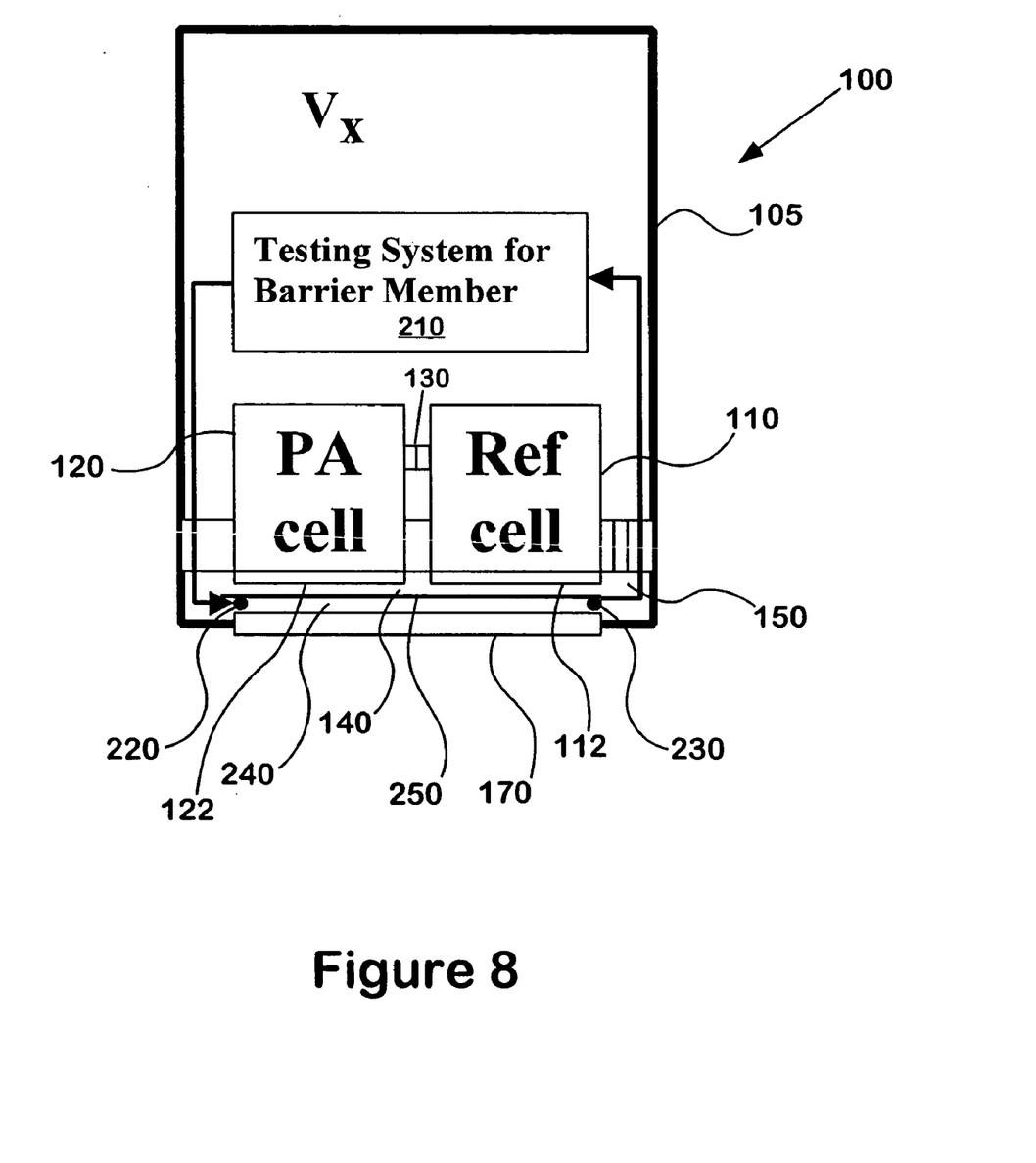
FIG. 8 shows another embodiment of a photoacoustic detector of the present invention.

As discussed above, background microphone 9 can be used alone or in addition to SDE volume $V_x$ to reduce noise level in the output signal of the photoacoustic sensor of the present invention. FIG. 8 illustrates another embodiment of the present invention in which the concept of directly measuring the noise in the output signal of a photoacoustic sensor 100 resulting from an incident external pressure wave is embodied in a reference cell 110. In the embodiment of FIG. 8, photoacoustic detector 100, includes a housing 105 that preferably defines an SDE volume $V_x$ as described above. Also within housing 105 are preferably a photoacoustic (PA) cell 120 and a reference (Ref) cell 110.

In general, a photoacoustic signal is output by only photoacoustic cell 120. Preferably, photoacoustic cell 120 and reference cell 110 are fabricated to be as similar or In general, a photoacoustic signal is output by only photoacoustic cell 120. Preferably, photoacoustic cell 120 and reference cell 110 are fabricated to be as similar or well matched as possible. For example, each of photoacoustic cell 120 and reference cell 110 preferably have the same volume. Each of photoacoustic cell 120 and reference cell 110 also preferably have the same internal components. For example, each of photoacoustic cell 120 and reference cell 110 may be equipped with a source of irradiation and a microphone as discussed above. By using the output signal from reference cell 110 as an offset for the output signal from photoacoustic cell 120 as described above, one can substantially reduce the noise in the output signal of photoacoustic detector 100 arising from external incident pressure waves.

Preferably, each of photoacoustic cell 120 and reference cell 110 can be coupled to a pressure gradient microphone 130. The output of microphone 130 is proportional to the pressure difference between photoacoustic cell 120 and reference cell 110. While the low frequency noise from external pressure fluctuations is the same in each of photoacoustic cell 120 and reference cell 110, there is a photoacoustic signal from photoacoustic cell 120 only. Measuring only the pressure difference between photoacoustic cell 120 and reference cell 110 substantially reduces or eliminates noise in the output signal resulting from external pressure fluctuations. Given the noise suppression provided by use of a reference measurement, porous member(s) 122 and 112 at the openings of photoacoustic cell 120 and reference cell 110, respectively, can be designed with greater porosity than in conventional photoacoustic sensors, leading to faster response.

In several studies using a reference cell configuration similar to that illustrated in FIG. 8, it was determined that the resultant noise reduction was excellent at relatively low frequency noise levels but decreased as frequency was increased. In that regard, the noise reduction results achieved with use of reference cell 110 is complementary to that achieved with SDE volume $V_x$, which exhibits low pass characteristics.

In that regard, photoacoustic detector 100 also includes SDE volume $V_x$. Each of photoacoustic cell 120 and reference cell 110 are in fluid communication with volume $V_x$ via, for example, a channel 140 that is in fluid communication with a port 150 to volume $V_x$. As described above, photoacoustic cell 120 is preferably provided with sinter disk 122 at the inlet thereof, while reference cell 110 is preferably provided with sinter disk 112 at the inlet thereof. Likewise another sinter disk 170 is preferably provided at the inlet of housing 105 through which all gas diffuses into the photoacoustic sensor 100.

Figure 9:
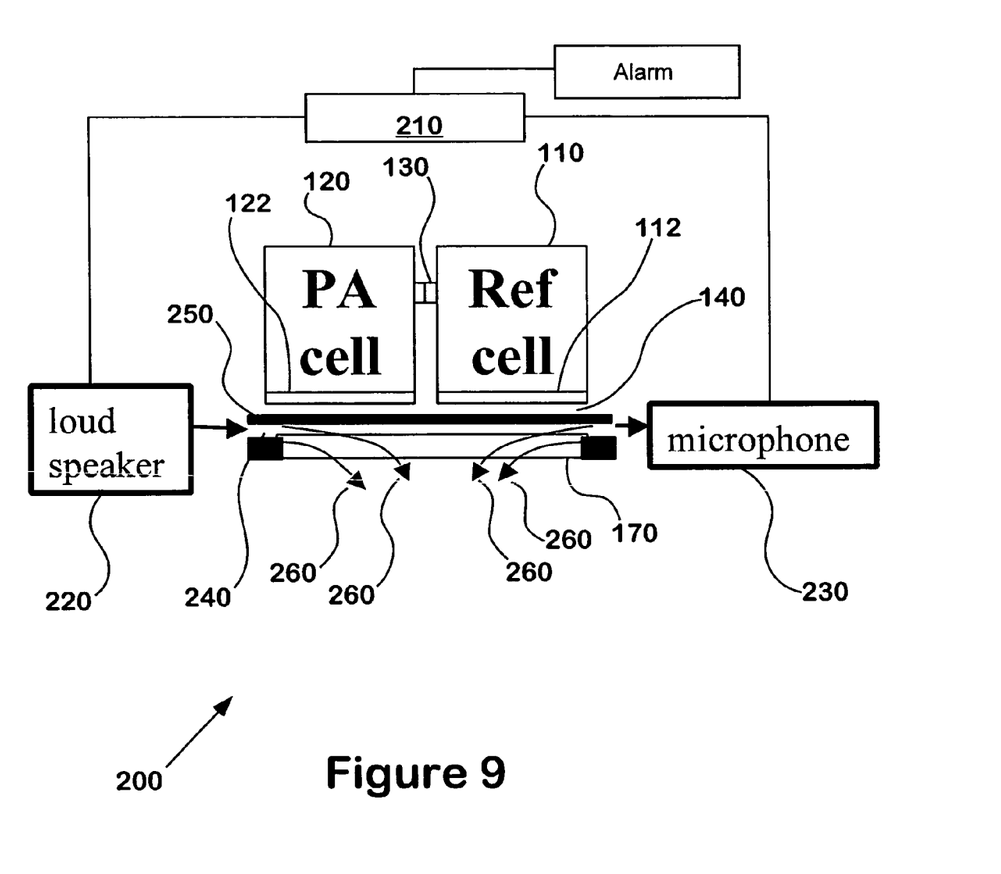
FIG. 9 shows a preferred embodiment of the photoacoustic detector of FIG. 8.

As shown in FIG. 9, photoacoustic sensor 100 is also preferably provided with a test system (for example, including system circuitry 210) to test the integrity of the outermost porous member (that is, sinter disk 170). In that regard, sinter disk 170 is in direct contact with ambient conditions and can, from time to time, become clogged with debris or contaminants that can prevent diffusion of gas into photoacoustic sensor 100. In general, the test system preferably includes a transmitter/source of sound/pressure waves 220 such as a loudspeaker and a sensor/receiver 230 such as a microphone for detecting sound/pressure waves created by source 220. Source 220 is preferably positioned on one side of a passage 240 created between outer porous member 170 and a pressure/acoustic tight membrane 250. In the embodiment of FIG. 8, acoustic tight membrane 250 also defines/bounds channel 140 as described above. The acoustic tight membrane 250 preferably offers a larger acoustic resistance to pressure waves generated by source 220 than the outer porous member 170 to prevent sound of the frequency used by source 220 from passing though acoustic tight membrane 250. This result may be achieved by using a membrane with a smaller pore size than the pore size of outer porous member 170. To maintain a fast response time, porous member 250 is preferably as thin as possible. In one embodiment, a GORETEX® membrane with a pore size of approximately 0.2 micron, a thickness of approximately 0.5 mm and a diameter of approximately 32 mm was used. The pore size of outer porous member 170 in this embodiment was approximately 5 microns.

The operation of the test system will be described briefly with reference to FIG. 8. In that regard, during a test of the integrity or condition of outer porous member 170, a sound/pressure wave signal is transmitted by transmitter 220. Pressure/acoustic tight membrane 250 preferably substantially prevents passage of sound/pressure waves of the frequency of the signal from transmitter 220 from passing therethrough and thus assists in transmitting the sound toward receiver 230 at the opposite end of passage 240. However, the frequency of the signal from transmitter 220 is preferably chosen so that it is at least partially transmittable through outer porous member 170. Thus, a base measurement output signal from receiver 230 corresponding to a signal from transmitter 220 of a certain amplitude and frequency can be taken, for example, when photoacoustic sensor 100 is new or "unclogged." The output signal from receiver 230 will reflect certain acoustic losses through porous member 170. This test procedure is preferably periodically repeated over the life of photoacoustic sensor 100. As outer porous member 170 becomes more clogged with debris from the environment(s) in which photoacoustic sensor 100 is used, acoustic losses therethrough will diminish and a correspondingly greater signal will be received by receiver 230. Preferably, a threshold limit (corresponding to an overly clogged porous member 170) for the output signal from receiver 230 is set so that circuitry 210 can test whether this threshold limit has been exceeded. If the threshold limit has been exceeded, circuitry 210 can trigger an alarm (for example, a visible or audible alarm) so that, for example, outer porous membrane 170 can be replaced. It is understood by those skilled in the art that use of this type of test system is not limited to photoacoustic sensors, but is equally applicable to the use of porous members (for example, metal sinter disks or porous membranes) in any sensor system, including those which use electrochemical or catalytic sensors.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A photoacoustic detector in fluid connection with an environment, comprising a measuring system to measure the photoacoustic excitation of an analyte gas entering the photoacoustic detector, a reference system to measure the effect of pressure waves in the environment, an electronic system for combining an output from the reference system with an output of the measuring system to offset noise resulting from pressure waves in the environment to generate an output signal of the photoacoustic detector, and wherein both the measuring system and the reference system are in fluid communication with the environment and an SDE volume such that the pressure readily equalizes between the measuring system, the reference system, and the SDE volume while the diffusion of the analyte gas into the SDE volume is hindered.

2. The photoacoustic detector of claim 1 wherein the measuring system includes a first microphone to measure photoacoustic excitation of the analyte gas and the reference system includes a second microphone to generate an offset signal that is processed by the electronic system to reduce the effect of externally generated pressure waves on the output signal of the photoacoustic sensor.

3. The photoacoustic detector of claim 2 wherein the first microphone is disposed within a photoacoustic cell and the second microphone is disposed within a reference cell, the photoacoustic cell and the reference cell being of generally the same volume.

* * * * *